(12) United States Patent
Ogawa et al.

(10) Patent No.: US 10,022,871 B2
(45) Date of Patent: Jul. 17, 2018

(54) MEDICAL SYSTEM AND CONTROL METHOD THEREFOR

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 198 days.

(21) Appl. No.: 15/000,341

(22) Filed: Jan. 19, 2016

(65) Prior Publication Data

US 2016/0128790 A1 May 12, 2016

Related U.S. Application Data

(63) Continuation of application No. PCT/JP2014/068853, filed on Jul. 16, 2014.

(30) Foreign Application Priority Data

Jul. 26, 2013 (JP) .................................. 2013-155884

(51) Int. Cl.
    *B25J 9/16*     (2006.01)
    *B25J 3/04*     (2006.01)
    (Continued)

(52) U.S. Cl.
    CPC ............. *B25J 9/1689* (2013.01); *A61B 34/30* (2016.02); *A61B 34/32* (2016.02); *A61B 34/37* (2016.02);
    (Continued)

(58) Field of Classification Search
    CPC ..... B25J 9/1689; B25J 3/04; B25J 3/00; B25J 9/0084; B25J 9/1669; A61B 34/30;
    (Continued)

(56) References Cited

U.S. PATENT DOCUMENTS 4,853,874 A * 8/1989 Iwamoto ................... B25J 3/04
    414/2
5,105,367 A * 4/1992 Tsuchihashi ............... B25J 3/04
    700/264
(Continued)

FOREIGN PATENT DOCUMENTS

EP     2324789 A1     5/2011
JP     2001-087281 A     4/2001
(Continued)

OTHER PUBLICATIONS

International Search Report dated Aug. 26, 2014 issued in PCT/JP2014/068853.
(Continued)

*Primary Examiner* — Bao Long T Nguyen
(74) *Attorney, Agent, or Firm* — Scully, Scott, Murphy & Presser, P.C.

(57) ABSTRACT

Provided is a medical system including a first slave arm; a master arm having a joint configuration with a structure similar to that of a joint configuration of the first slave arm; a second slave arm; a manipulation-target switching unit that switches a manipulation target to be manipulated with the master arm between the slave arms; and a controller that is capable of switching between a first control mode and a second control mode in accordance with the joint configuration of the slave arm to be controlled. The first control mode is a mode for controlling rotation of joints of the first slave arm on the basis of rotation amounts of joints of the master arm. The second control mode is a mode for controlling rotation of joints of the second slave arm on the basis of a movement of a predetermined section of the master arm.

11 Claims, 13 Drawing Sheets

(51) Int. Cl.
*A61B 34/37* (2016.01)
*A61B 34/30* (2016.01)
*A61B 34/32* (2016.01)
*A61B 34/00* (2016.01)
*A61B 90/00* (2016.01)
*A61B 34/20* (2016.01)

(52) U.S. Cl.
CPC .............. *A61B 34/74* (2016.02); *B25J 3/04* (2013.01); *A61B 2034/2059* (2016.02); *A61B 2034/301* (2016.02); *A61B 2090/067* (2016.02); *Y10S 901/02* (2013.01); *Y10S 901/28* (2013.01)

(58) Field of Classification Search
CPC ......... A61B 34/32; A61B 34/37; A61B 34/74; A61B 2034/2059; A61B 2034/301; A61B 2090/067; A61B 2090/061; A61B 34/70; A61B 34/35; Y10S 901/02; Y10S 901/28; G05B 2219/40399; G05B 2219/40405; G05B 2219/40407; G05B 2219/40182
USPC .............. 700/245, 247, 250, 257; 901/2, 28; 318/568.17
See application file for complete search history.

(56) References Cited

U.S. PATENT DOCUMENTS

| | | | | |
|---|---|---|---|---|
| 5,876,325 | A * | 3/1999 | Mizuno | A61B 1/00048 600/102 |
| 6,364,888 | B1 * | 4/2002 | Niemeyer | B25J 3/04 348/E13.014 |
| 2002/0082612 | A1 | 6/2002 | Moll et al. | |
| 2002/0128552 | A1 * | 9/2002 | Nowlin | A61B 34/70 600/427 |
| 2003/0013949 | A1 | 1/2003 | Moll et al. | |
| 2003/0216715 | A1 | 11/2003 | Moll et al. | |
| 2004/0039485 | A1 | 2/2004 | Niemeyer et al. | |
| 2009/0171374 | A1 * | 7/2009 | Omori | A61B 34/71 606/130 |
| 2011/0137322 | A1 | 6/2011 | Moll et al. | |
| 2012/0059392 | A1 | 3/2012 | Diolaiti | |
| 2012/0059519 | A1 | 3/2012 | Kishi | |
| 2012/0130399 | A1 | 5/2012 | Moll et al. | |
| 2012/0191247 | A1 | 7/2012 | Kishi | |
| 2013/0304256 | A1 | 11/2013 | Moll et al. | |
| 2013/0325029 | A1 * | 12/2013 | Hourtash | B25J 9/1607 606/130 |
| 2013/0325030 | A1 * | 12/2013 | Hourtash | B25J 9/1607 606/130 |
| 2014/0148818 | A1 * | 5/2014 | Komuro | A61B 18/1402 606/130 |
| 2014/0195048 | A1 | 7/2014 | Moll et al. | |
| 2014/0229007 | A1 * | 8/2014 | Kishi | A61B 19/2203 700/257 |
| 2016/0045272 | A1 | 2/2016 | Diolaiti | |

FOREIGN PATENT DOCUMENTS

| | | |
|---|---|---|
| JP | 3583777 B2 | 11/2004 |
| JP | 2005-131417 A | 5/2005 |
| JP | 2009-539573 A | 11/2009 |
| JP | 2010-524547 A | 7/2010 |
| JP | 4608601 B2 | 1/2011 |
| JP | 2012-055996 A | 3/2012 |
| JP | 2012-071406 A | 4/2012 |
| JP | 2012-148379 A | 8/2012 |
| WO | WO 93/13916 A1 | 7/1993 |
| WO | 00/030548 A1 | 6/2000 |
| WO | WO 2007/146987 A2 | 12/2007 |
| WO | WO 2009/044287 A2 | 4/2009 |

OTHER PUBLICATIONS

Extended Supplementary European Search Report dated Mar. 2, 2017 in European Patent Application No. 14 82 9426.7.

* cited by examiner

FIG. 5
LEFT AND RIGHT SLAVE ARMS
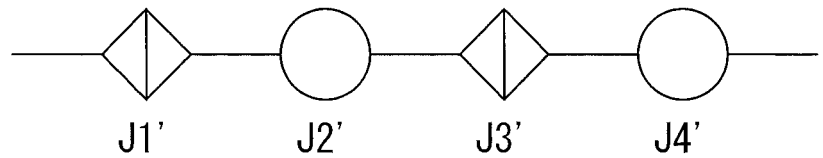
LEFT AND RIGHT MASTER ARMS
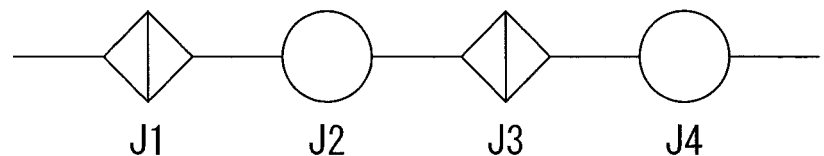

FIG. 11
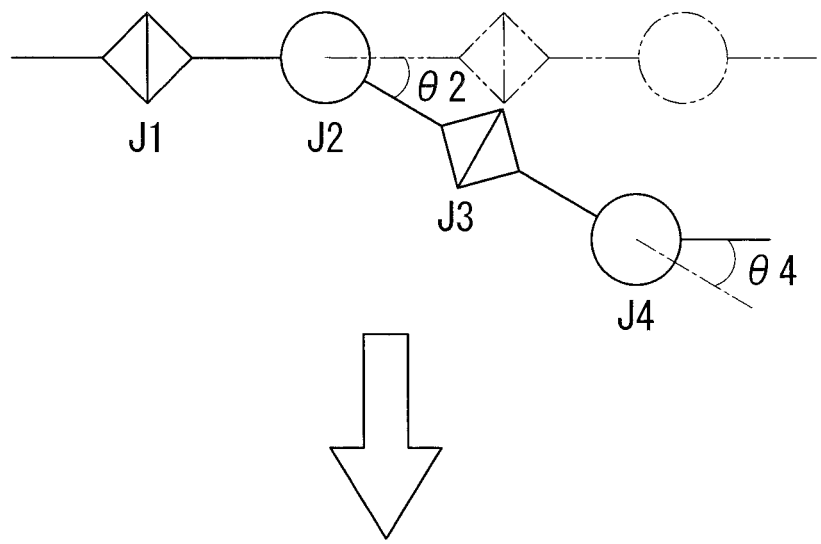
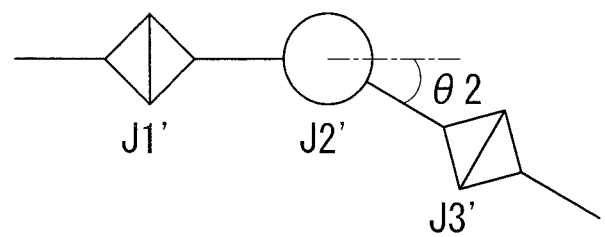

MEDICAL SYSTEM AND CONTROL METHOD THEREFOR

CROSS-REFERENCE TO RELATED APPLICATIONS

This is a continuation of International Application PCT/JP2014/068853, with an international filing date of Jul. 16, 2014, which is hereby incorporated by reference herein in its entirety. This application claims the benefit of Japanese Patent Application No. 2013-155884, filed on Jul. 26, 2013, the content of which is incorporated herein by reference.

TECHNICAL FIELD

The present invention relates to medical systems and control methods therefor.

BACKGROUND ART

In the related art, as an example of an operation input device for remotely controlling a slave arm having joints, there is a known medical system equipped with a master arm having a joint configuration with a structure similar to that of a joint configuration of a slave arm (for example, see Patent Literatures 1 and 2). With such a system, since the slave arm can be made to reproduce a movement corresponding to the movement of the master arm, an operator can intuitively manipulate the slave arm while directly recognizing the shape and movement of the slave arm from the shape and movement of the master arm.

Another known medical system includes a single slave arm and multiple types of distal-end treatment sections that are attachable to the arm. In such a medical system, an operable section can be replaced according to the type of distal-end treatment section to be used (for example, see Patent Literature 3).

The distal end of a slave arm is provided with a distal-end treatment section, such as forceps, scissors, or a hook electrode. In an actual surgical operation, different types of slave arms equipped with distal-end treatment sections for different purposes are often used in an interchanging manner. In addition to different types of distal-end treatment sections, it is also desirable to use multiple types of slave arms with different joint configurations, that is, different operating ranges and different degrees of freedom of motion. In Patent Literatures 1 and 2, the joint configuration of the master arm and the joint configuration of the slave arm have a one-to-one correspondence relationship.

With regard to Patent Literature 3, multiple types of distal-end treatment sections can be used in an interchanging manner. However, it is necessary to prepare operable sections equal in number to the number of types of distal-end treatment sections, and an operable section has to be replaced every time a distal-end treatment section is replaced. Furthermore, in Patent Literature 3, the shape of a distal-end treatment section and the shape of a grip section at the master side are simply matched, and the use of slave arms having different joint configurations is not taken into account.

CITATION LIST

Patent Literature

{PTL 1}
Publication of Japanese Patent No. 3583777
{PTL 2}
Publication of Japanese Patent No. 4608601
{PTL 3}
Japanese Unexamined Patent Application, Publication No. 2001-87281

SUMMARY OF INVENTION

A first aspect of the present invention provides a medical system including a first slave arm having joints; a master arm that has a joint configuration with a structure similar to a joint configuration of the first slave arm and that is operated by an operator; a second slave arm having joints; a manipulation-target switching unit that switches a manipulation target to be manipulated with the master arm between the first slave arm and the second slave arm; and a controller that controls the first slave arm and the second slave arm on the basis of an operation performed on the master arm. The controller switches between a first control mode and a second control mode in accordance with the joint configuration of the slave arm selected by the manipulation-target switching unit. The first control mode is a mode for controlling rotation of the joints of the first slave arm on the basis of rotation amounts of joints of the master arm so that the first slave arm has a shape similar to a shape of the master arm, and the second control mode is a mode for controlling rotation of the joints of the second slave arm on the basis of a movement of a predetermined section of the master arm so as to cause a predetermined section of the second slave arm to follow the movement of the predetermined section of the master arm.

A second aspect of the present invention provides a control method for a medical system having a plurality of slave arms each having joints and a master arm operated by an operator. The control method includes alternately selecting a manipulation target to be manipulated with the master arm from among the plurality of slave arms; and switching between a first control mode and a second control mode in accordance with whether or not a joint configuration of the selected slave arm and a joint configuration of the master arm have structures similar to each other. The first control mode is a mode for controlling rotation of joints of the slave arm on the basis of rotation amounts of joints of the master arm so that the slave arm has a shape similar to a shape of the master arm. The second control mode is a mode for controlling the rotation of the joints of the slave arm on the basis of a movement of a predetermined section of the master arm so as to cause a predetermined section of the slave arm to follow the movement of the predetermined section of the master arm.

BRIEF DESCRIPTION OF DRAWINGS

FIG. 5 schematically illustrates joint configurations of left and right slave arms and left and right master arms.

FIG. 11 illustrates the movement of the slave arms according to a first modification of the second control mode.

DESCRIPTION OF EMBODIMENT

A medical system 100 according to an embodiment of the present invention will be described below with reference to the drawings.

Figure 1:
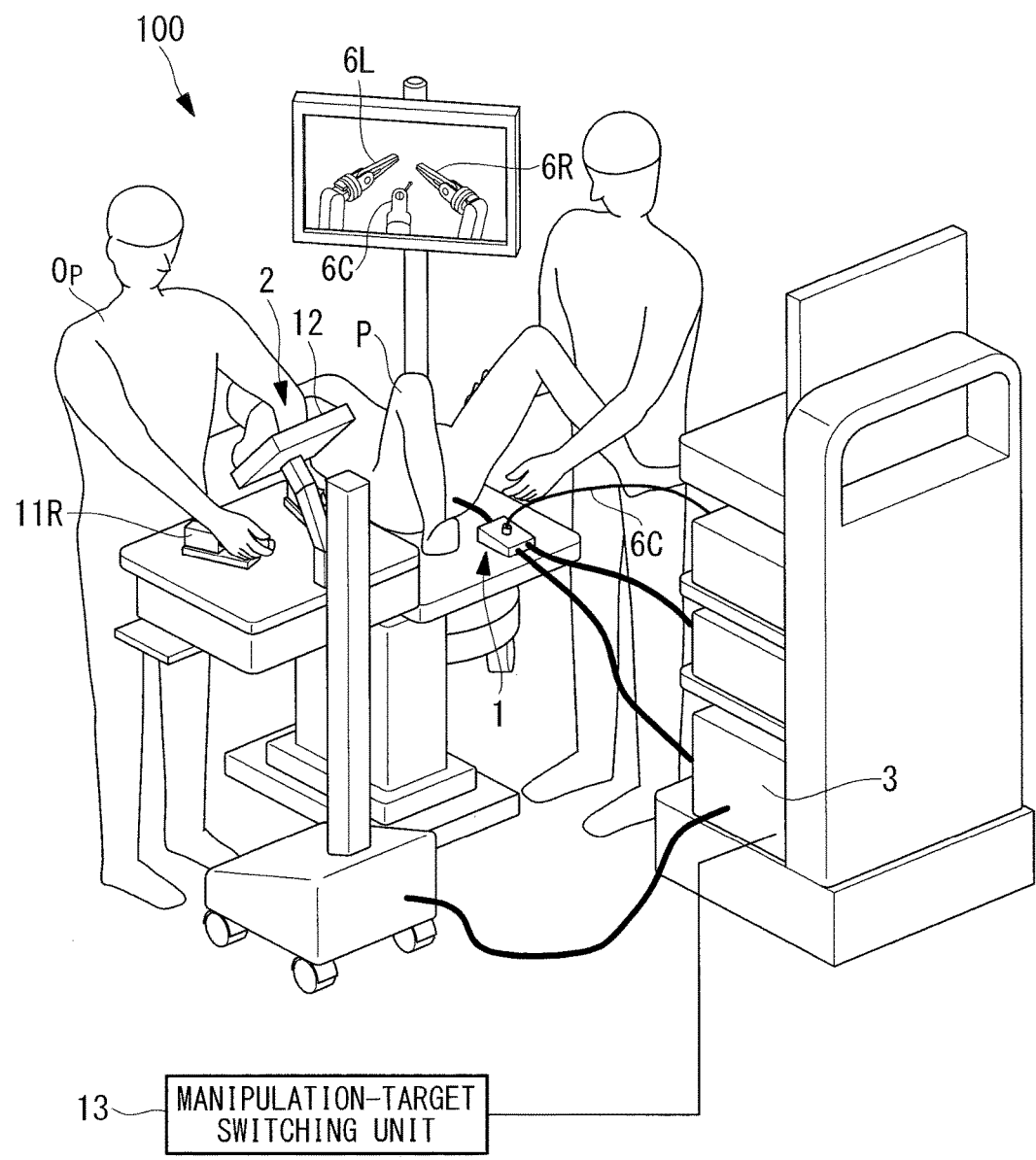
FIG. 1 is an external view illustrating the overall configuration of a medical system according to an embodiment of the present invention.

As shown in FIG. 1, the medical system 100 according to this embodiment includes a slave manipulator 1 to be inserted into the body of a patient P, and an operation input unit 2 and a controller 3 that are disposed in the vicinity of a surgical table on which the patient P lies.

A general overview of the medical system 100 will be described first. The distal end of the slave manipulator 1 is provided with an endoscope 5 and slave arms 6L, 6R, and 6C, which will be described later. When an operator Op inserts the slave manipulator 1 into the body of the patient P through his/her anus and operates the operation input unit 2 while observing an internal body image acquired by the endoscope 5 and displayed on a display 12 provided on the operation input unit 2, the controller 3 controls the slave manipulator 1 on the basis of an operation input to the operation input unit 2. Thus, the operator Op can remotely control the slave manipulator 1 located inside the body and perform a medical treatment inside the body by using the slave arms 6L, 6R, and 6C provided in the slave manipulator 1.

Next, the components of the medical system 100 will be described in detail.

Figure 2:
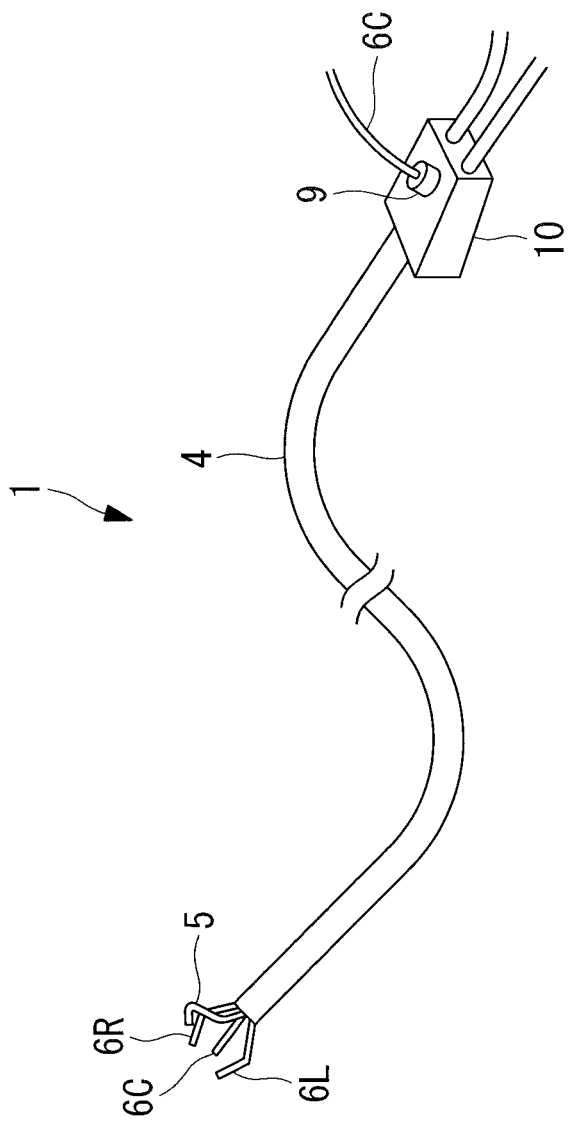
FIG. 2 illustrates the overall configuration of a manipulator included in the medical system in FIG. 1.

As shown in FIG. 2, the slave manipulator 1 includes an elongated flexible section 4 to be inserted into the body, and the endoscope 5 and the three slave arms 6L, 6R, and 6C, which are provided at the distal end of the flexible section 4.

Although the description of this embodiment relates to the slave manipulator 1 having flexibility, the slave manipulator 1 may alternatively have a rigid insertion section in place of the flexible section 4.

Figure 3:
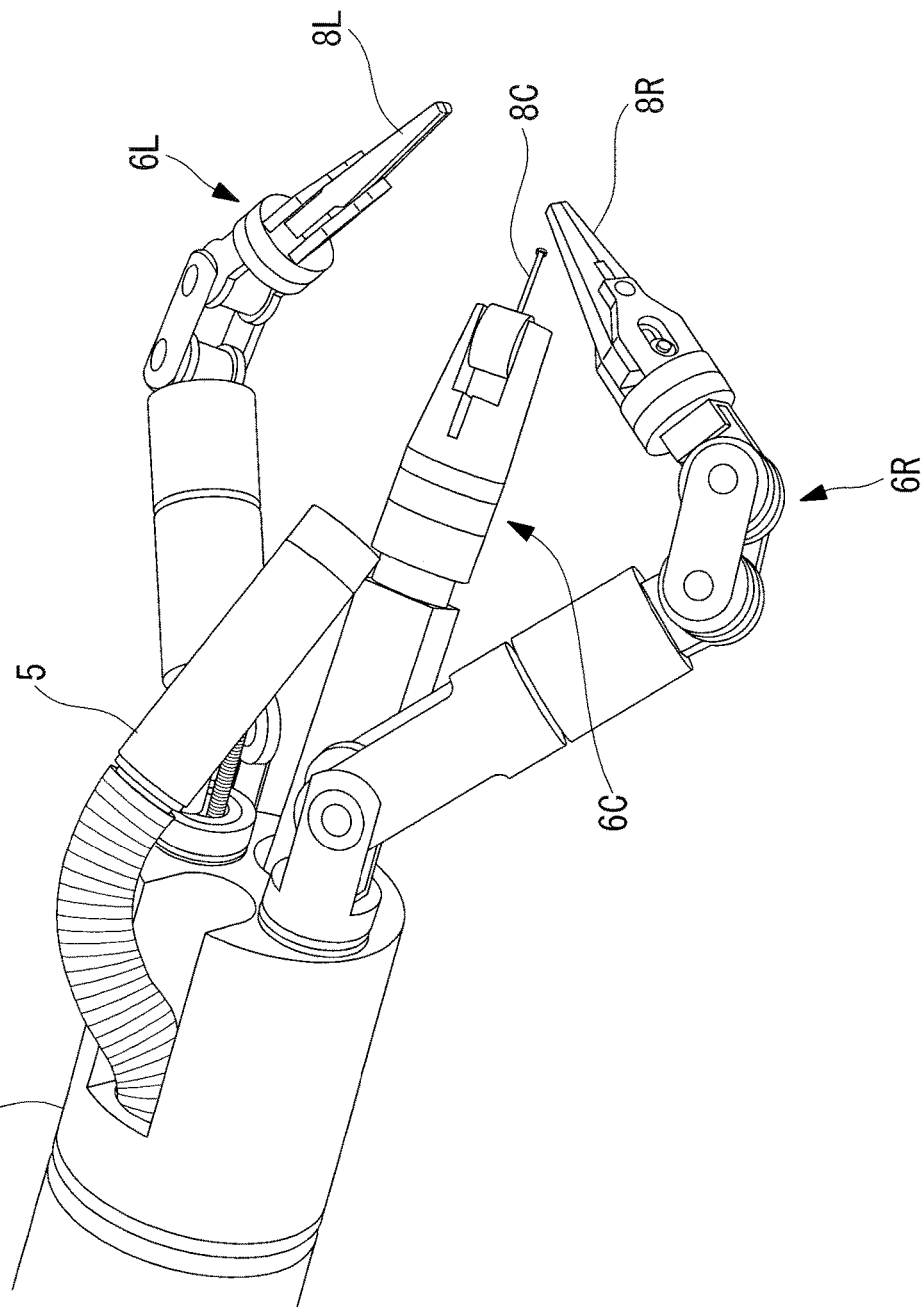
FIG. 3 is an external view illustrating a distal-end portion of the manipulator in FIG. 2.

FIG. 3 is an external view illustrating the distal end portion of the slave manipulator 1.

As shown in FIG. 3, by bending the distal end portion of the endoscope 5 into a substantially S shape, the endoscope can acquire a bird's-eye-view image of the three slave arms 6L, 6R, and 6C arranged in the radial direction of the flexible section 4.

Two of the three slave arms are the left slave arm (first slave arm) 6L and the right slave arm (first slave arm) 6R, which are provided at the distal end of the flexible section 4. The distal ends of these slave arms 6L and 6R are respectively provided with distal-end treatment sections 8L and 8R (e.g., forceps for gripping biological tissue).

The one remaining slave arm is an arbitrary slave arm (second slave arm) 6C disposed at the distal end of the flexible section 4 via a channel (not shown) formed in the flexible section 4. The channel extends from the distal end of the flexible section 4 to a port 9 provided at the base end of the flexible section 4. The central slave arm 6C inserted into the channel through the port 9 protrudes from a channel opening formed between the left slave arm 6L and the right slave arm 6R so as to be disposed between the right slave arm 6R and the left slave arm 6L. Similar to the left and right slave arms 6L and 6R, the distal end of the slave arm 6C is provided with a distal-end treatment section 8C (e.g., electric scalpel).

The three slave arms 6L, 6R, and 6C branch off at a branch section 10 where the aforementioned port 9 is provided, and are individually connected to the controller 3, as shown in FIG. 1.

In this example, the left and right slave arms 6L and 6R are described as being arms provided at the distal end of the flexible section 4. Alternatively, similarly to the central slave arm 60 described above, the left and right slave arms 6L and 6R may protrude from openings of channels, such that multiple slave arms are interchangeable by being inserted into and removed from the channels.

The operation input unit 2 includes two master arms 11L and 11R and the display 12.

Figure 4:
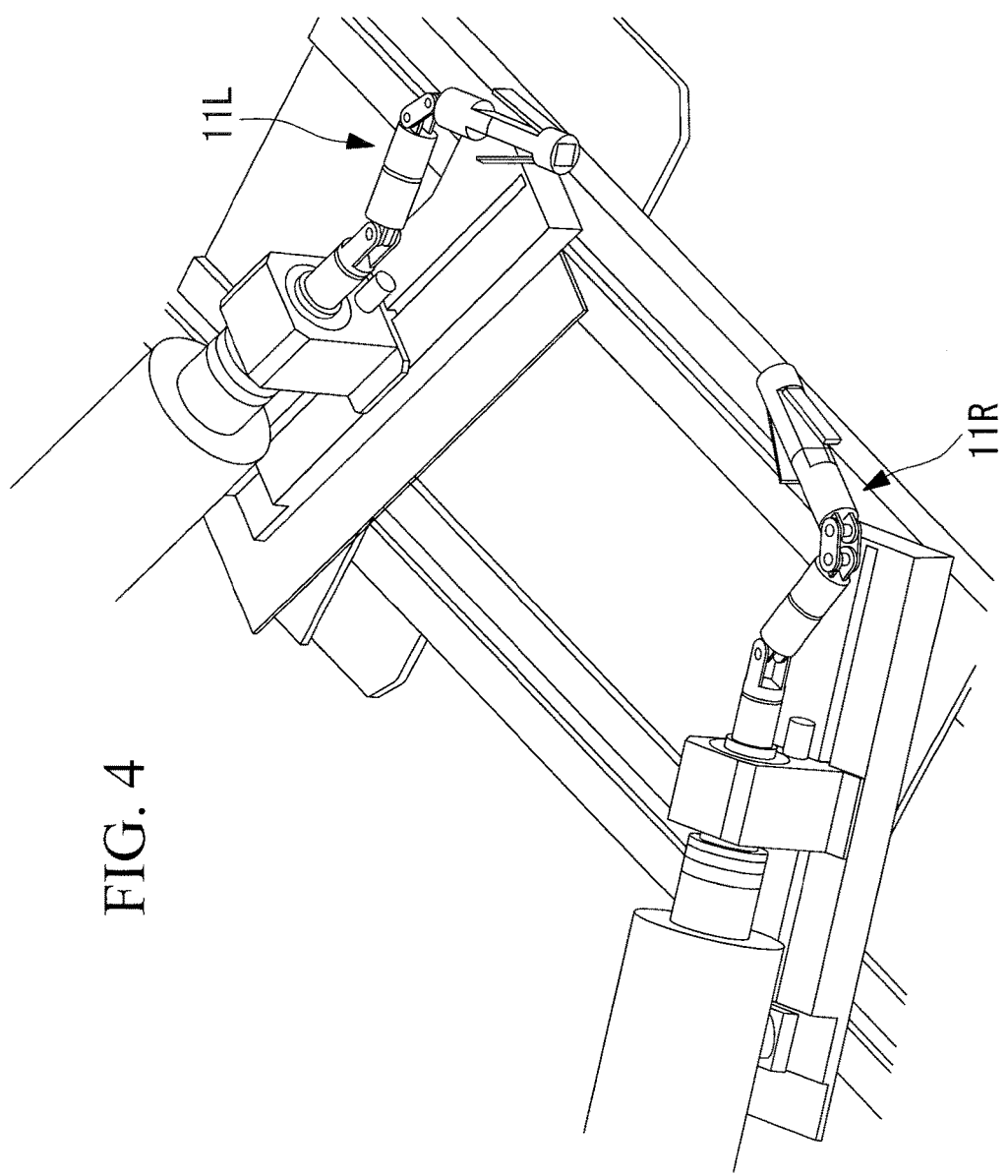
FIG. 4 is an external view illustrating master arms included in an operation input unit in FIG. 1.

As shown in FIG. 4, the master arms include a left master arm 11L corresponding to the left slave arm 6L and a right master arm 11R corresponding to the right slave arm 6R.

FIG. 5 schematically illustrates joint configurations of the left and right slave arms 6L and 6R and the left and right master arms 11L and 11R. As shown in FIG. 5, each master arm 11L or 11R has a joint configuration with a structure similar to that of a joint configuration of the corresponding slave arm 6L or 6R.

In this example, each of the slave arms 6L and 6R has a roll joint J1', a yaw joint J2', a roll joint J3', and a yaw joint J4' in this order from the base end. Likewise, each of the master arms 11L and 11R has a roll joint J1, a yaw joint J2, a roll joint J3, and a yaw joint J4 in this order from the base end. The roll joints J1', J3', J1, and J3 rotate about roll axes extending from the base ends to the distal ends of the respective arms 6L, 6R, 11L, and 11R in the longitudinal direction of the arms 6L, 6R, 11L, and 11R. The yaw joints J2', J4', J2, and J4 rotate about yaw axes extending orthogonally to the roll axes (i.e., extending orthogonally to the plane of the drawing in FIG. 5). Furthermore, the ratio of distances between neighboring joints is the same between the left slave arm 6L and the left master arm 11L, and the ratio of distances between neighboring joints is the same between the right slave arm 6R and the right master arm 11R.

The joints Ji (i=1, 2, 3, 4) of each master arm 11L or 11R are individually provided with angle detectors, such as encoders. The operation input unit 2 detects amounts of change θi (i=1, 2, 3, 4) in the angles of the joints Ji by using the angle detectors and outputs the four detected amounts of change θi as operation signals to the controller 3.

Based on the operation signals of the master arms 11L and 11R received from the operation input unit 2, the controller 3 generates drive signals for driving the joints Ji' of the slave arms 6L, 6R, and 6C and transmits the generated drive signals to the slave manipulator 1. The slave manipulator 1 rotates the joints Ji' in accordance with control signals so as to move the slave arms 6L, 6R, and 6C.

Furthermore, the medical system 100 according to this embodiment includes a manipulation-target switching unit 13 for changing manipulation targets to be manipulated with the master arms 11L and 11R. For example, the manipulation-target switching unit 13 is a switch that is provided in the operation input unit 2 and that is to be operated by the operator Op. The manipulation-target switching unit 13 switches a manipulation target to be manipulated with the left master arm 11L between the left slave arm 6L and the central slave arm 6C, and switches a manipulation target to be manipulated with the right master arm 11R between the right slave arm 6R and the central slave arm 6C.

With regard to this manipulation-target switching operation, the operator Op may preliminarily set switch targets, such that when the operator Op presses the switch, the manipulation targets are switched to the switch targets preset as default. Alternatively, the operator Op may switch between the currently-used slave arm and a slave arm to be used next, which are switch targets, by setting the switch targets using, for example, an operating panel.

Signals indicating the slave arms selected by the manipulation-target switching unit 13 are transmitted to the controller 3. The controller 3 sets the manipulation targets to be manipulated with the master arms 11L and 11R to the slave arms 6L, 6R, 6C designated by the received signals. Specifically, if the operator Op desires to manipulate the central slave arm 6C, the operator Op uses the manipulation-target switching unit 13 to switch the manipulation target to be manipulated with one of the left and right master arms 11L and 11R to the central slave arm 6C, so that the central slave arm 6C can be manipulated by using the left master arm 11L or the right master arm 11R.

In this case, the controller 3 selects a first control mode or a second control mode in accordance with whether or not the joint configurations of the slave arms 6L, 6R, 6C selected by the manipulation-target switching unit 13 have structures substantially similar to those of the joint configurations of the corresponding master arms 11L and 11R, and controls the slave arms 6L, 6R, 6C in accordance with the selected mode. Next, a method of controlling the slave manipulator 1 with the controller 3 will be described in detail.

Figure 6:
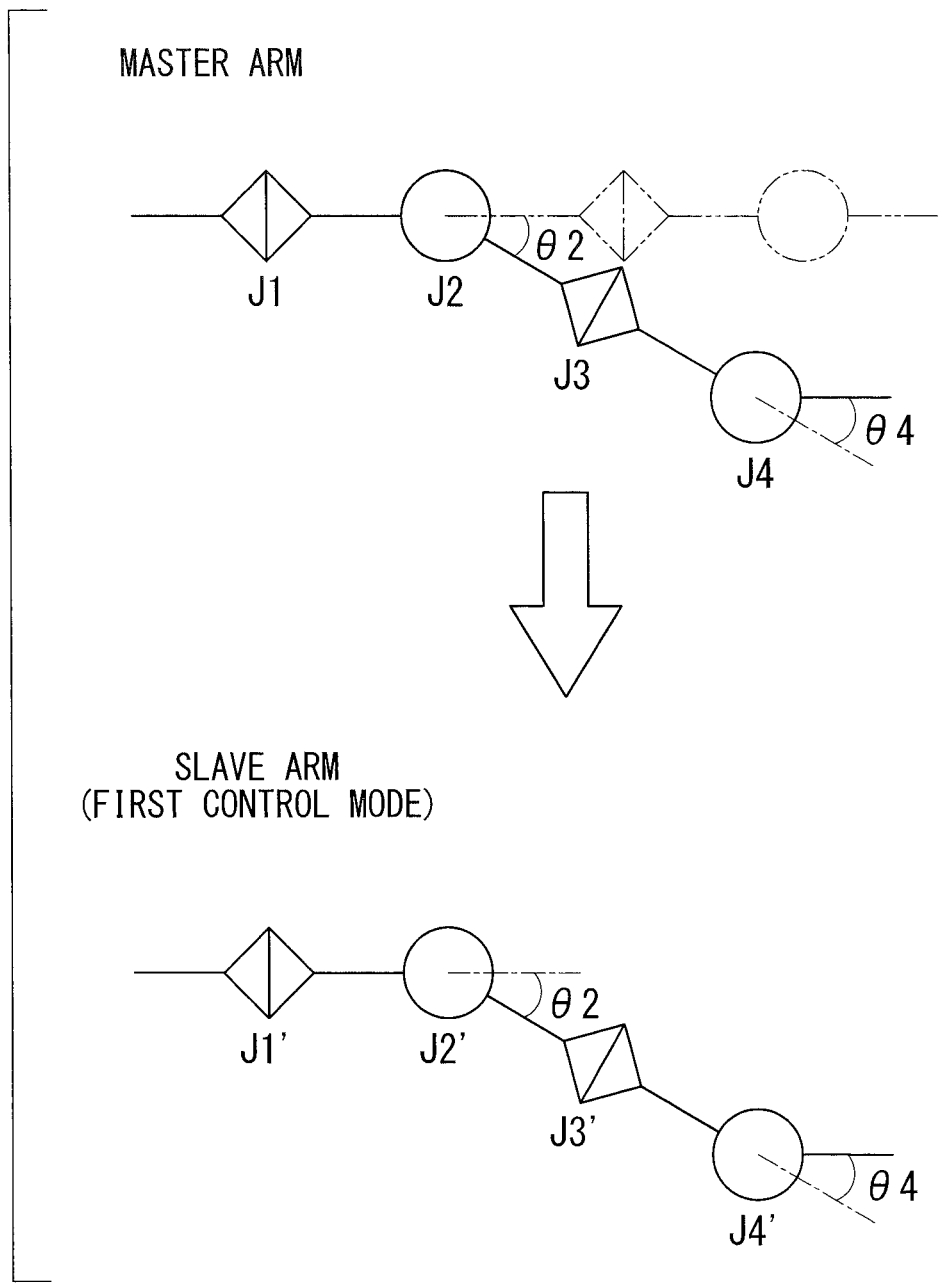
FIG. 6 illustrates the movement of the slave arms in FIG. 5 in a first control mode.

In the first control mode, the left and right slave arms 6L and 6R in their entirety are made to follow the movements of the entire left and right master arms 11L and 11R. Specifically, as shown in FIG. 6, the controller 3 rotates the joints Ji' of the slave arms 6L and 6R by amounts equal to the amounts of change θi in the joints Ji of the master arms 11L and 11R.

If the left slave arm 6L is selected by the manipulation-target switching unit 13 as a manipulation target to be manipulated with the left master arm 11L, the controller 3 controls the left slave arm 6L in accordance with the first control mode. Likewise, if the right slave arm 6R is selected by the manipulation-target switching unit 13 as a manipulation target to be manipulated with the right master arm 11R, the controller 3 controls the right slave arm 6R in accordance with the first control mode.

Figure 7:
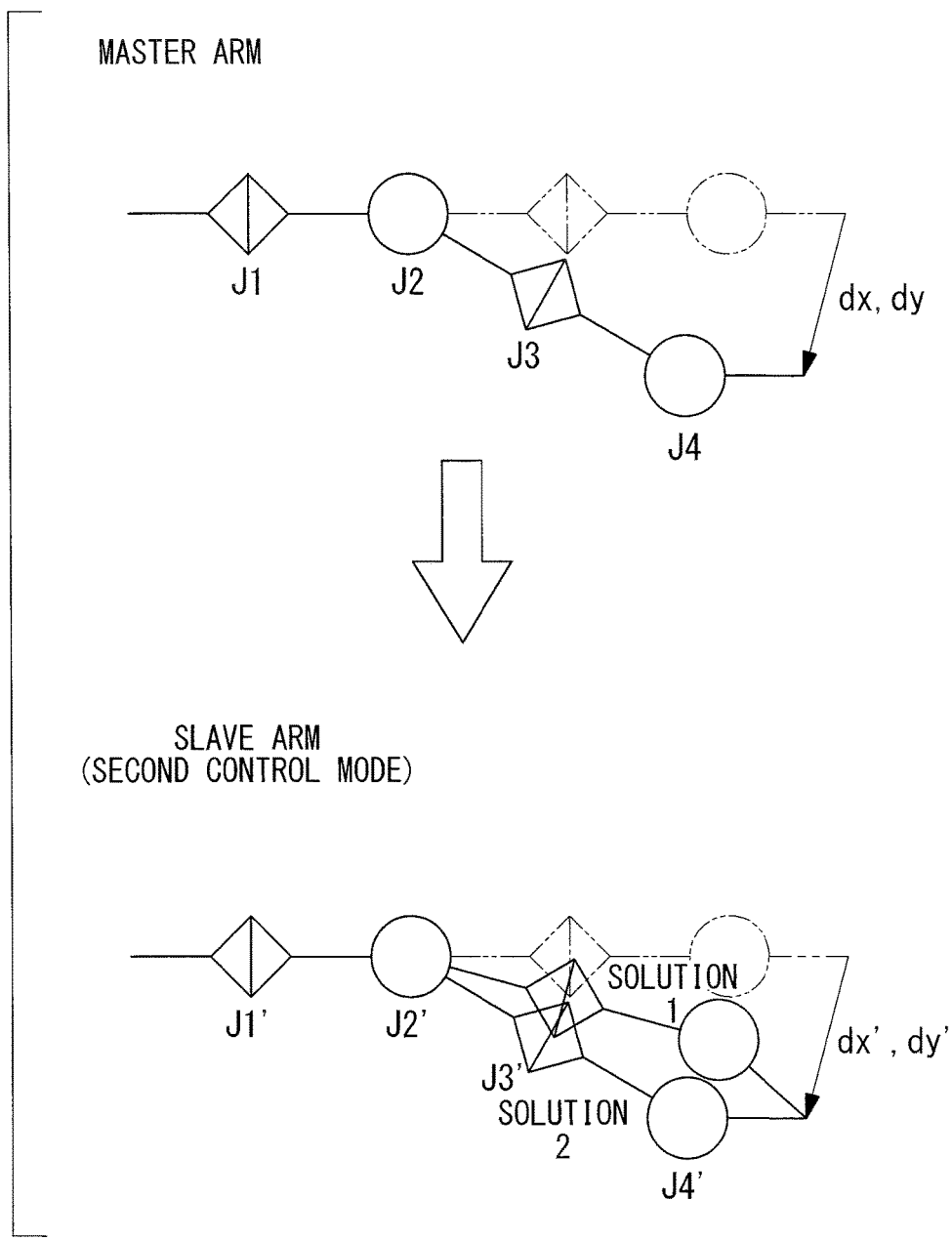
FIG. 7 illustrates the movement of the slave arms in FIG. 5 in a second control mode.

In the second control mode, the distal end of the central slave arm 6C is made to follow the movement of the distal end of the left or right master arm 11L or 11R. Specifically, the controller 3 uses the amounts of change θi in the joints Ji received from the operation input unit 2 to calculate the forward kinematics of the master arm 11L or 11R, thereby calculating movement amounts dx and dy, in respective directions, of the distal end of the master arm 11L or 11R in an operational coordinate system of the master arm 11L or 11R, as shown in FIG. 7. Then, the controller 3 converts the obtained movement amounts dx and dy into movement amounts dx' and dy', in respective directions, in an operational coordinate system of the central slave arm 6C. The coordinate conversion in this case is desirably performed such that the moving direction of the central slave arm 6C displayed on the display 12 observed by the operator Op matches the moving direction of the master arm 11L or 11R. Subsequently, the controller 3 calculates the reverse kinematics of the slave arm 6C on the basis of the obtained movement amounts dx' and dy' so as to calculate rotation amounts θi' of the joints Ji', and rotates the joints Ji' of the slave arm 6C by the obtained rotation amounts θi'.

In the reverse kinematics, since there may be multiple combinations of rotation amounts θi' for moving the distal end of the slave arm 6C by the movement amounts dx' and dy', as shown in FIG. 7, there is a possibility that multiple solutions of the reverse kinematics may be obtained. In FIG. 7, two solutions (i.e., solution 1 and solution 2) are shown as examples. If multiple solutions are obtained, the controller 3 employs the solution that gives the slave arm 6C a shape similar to that of the master arm 11L or 11R. If there are no solutions that give a similar shape, the controller 3 employs the solution with which the overall shape of the slave arm 6C is most similar to the overall shape of the master arm 11L or 11R (i.e., solution 2 in the example in FIG. 7), such as the solution corresponding to a minimum total of differences in rotational angles between corresponding joints Ji and Ji'.

With regard to each slave arm having a possibility of being used as the central slave arm 6C, the controller 3 stores, for each slave arm 6C, information related to the joint configuration thereof and a calculation expression, based on that information, to be used for the reverse kinematics, and selects and uses the calculation expression corresponding to the slave arm inserted in the channel. The slave arm inserted in the channel is recognized by a recognizing means (not shown).

In FIG. 7, the central slave arm 6C shown has a joint configuration with a structure substantially similar to that of the joint configuration of the master arm 11L or 11R for simplifying the description. However, the joint configuration of the central slave arm 6C is arbitrary; the central slave arm 6C used may have various kinds of joint configurations, as shown in FIGS. 11 to 14B, to be described later.

Furthermore, in this embodiment, the configuration that switches the manipulation targets between the left and right slave arms 6L and 6R and the central slave arm 6C has been described as an example. Alternatively, for example, when the right slave arm 6R is replaced with a new one by being removed from the flexible section 4, the control-mode switching operation may be performed on the basis of the joint configuration of the new slave arm. The same applies to the left slave arm 6L. Moreover, for example, when the endoscope 5 rotates by 180 degrees and the left and right positions of the slave arms 6L and 6R displayed on the display 12 are interchanged, the same method may be used if it is desired to interchange the left and right positions of the manipulation targets to be manipulated with the master arms 11L and 11R.

Next, the operation of the medical system 100 having the above-described configuration will be described with reference to FIGS. 8 to 10.

In order to perform a medical treatment inside the body of the patient P by using the medical system 100 according to this embodiment, the flexible section 4 of the slave manipulator 1 is inserted into the body of the patient P. While observing an internal body image acquired by the endoscope 5 with the display 12, the distal end of the slave manipulator 1 is moved to the vicinity of an affected area. Then, while observing the image displayed on the display 12, the operator Op manipulates the master arms 11L and 11R to move the slave arms 6L and 6R, thereby performing, for example, a pretreatment, which is necessary for medically treating the affected area, on the affected area and a surrounding area thereof.

Figure 8:
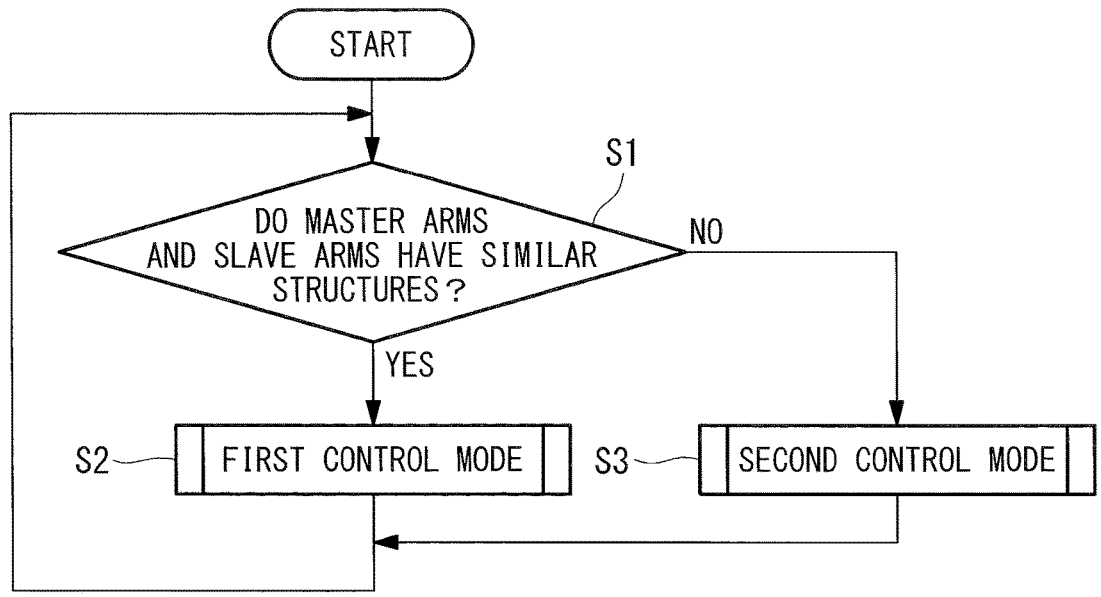
FIG. 8 is a flowchart illustrating a method of controlling the manipulator with a controller of the medical system in FIG. 1.
Figure 9:
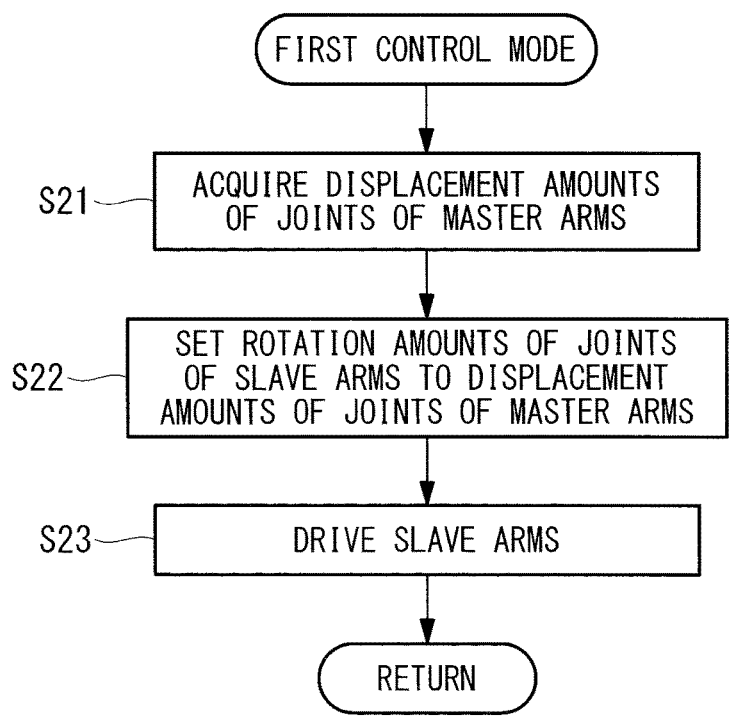
FIG. 9 is a flowchart illustrating a first control mode routine in FIG. 8.

In this case, as shown in FIG. 8, the left and right slave arms 6L and 6R are controlled in accordance with the first control mode (YES in step S1, and step S2). As shown in FIG. 9, in the first control mode, the joints Ji' of the slave arms 6L and 6R are rotated by the same amounts as the joints Ji of the master arms 11L and 11R (steps S21 and S22), so that the slave arms 6L and 6R in their entirely follow the movements of the entire master arms 11L and 11R (step S23). Specifically, because the overall shapes and orientations of the master arms 11L and 11R correspond to the overall shapes and orientations of the slave arms 6L and 6R, the operator Op can intuitively manipulate the left and right slave arms 6L and 6R while directly recognizing the current shapes and orientations of the slave arms 6L and 6R from the master arms 11L and 11R.

Subsequently, if the operator Op desires to medically treat a target site by changing to the central slave arm 6C, such as an electric scalpel, for example, the operator Op switches the manipulation target to be manipulated with the right master arm 11R to the central slave arm 6C by using the manipulation-target switching unit 13. Thus, the central slave arm 6C becomes capable of being moved by using the right master arm 11R. In this case, the controller 3 switches the first control mode to the second control mode on the basis of joint-configuration information about the switched slave arm 6C (NO in step S1) and controls the central slave arm 6C in accordance with the second control mode (step S3).

Figure 10:
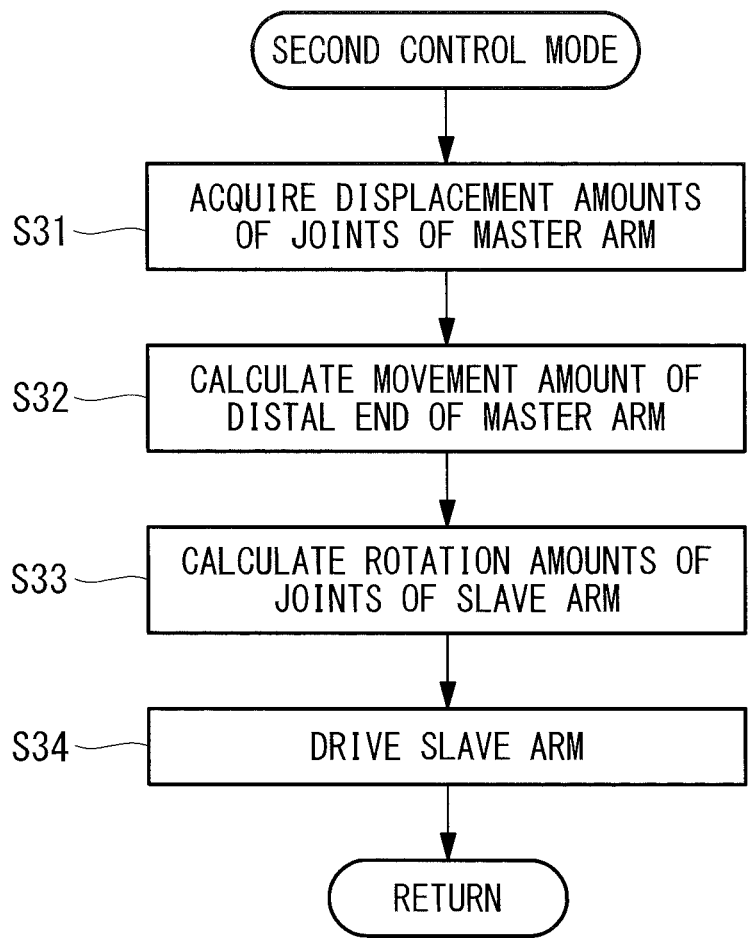
FIG. 10 is a flowchart illustrating a second control mode routine in FIG. 8.

As shown in FIG. 10, in the second control mode, the slave arm 6C is controlled on the basis of the movement of the distal end of the right master arm 11R (steps S31 and S32) so that the distal end of the central slave arm 6C follows the movement of the distal end of the right master arm 11R (steps S33 and S34). In this case, if multiple solutions are obtained in the reverse kinematics calculation in step S33, the solution that corresponds to a shape similar to that of the right master arm 11R is selected. Therefore, the operator Op can intuitively manipulate the distal end of the central slave arm 6C by using the right master arm 11R while roughly ascertaining the changing shape of the central slave arm 6C from the shape of the right master arm 11R.

According to this embodiment, the manipulation targets to be manipulated with the left and right master arms 11L and 11R can be switched between the two slave arms 6L and 6R or between the two slave arms 6R and 6C, and the central slave arm 6C having a structure not similar to those of the master arms 11L and 11R is controlled in accordance with the second control mode in which the distal end of the central slave arm 6C is made to follow the movement of the distal end of the master arm 11L or 11R. Accordingly, slave arms having any kind of joint configuration can be intuitively manipulated by using the left and right master arms 11L and 11R. Moreover, since it is not necessary to provide a dedicated master arm for each slave arm, the device configuration is simplified, thereby reducing manufacturing costs, as well as achieving a highly-versatile design.

In particular, because the left and right slave arms 6L and 6R located at the radially outer sides of the flexible section 4 are adjacent to surrounding tissue, the operator Op constantly needs to be aware of the bent shapes of the slave arms 6L and 6R, especially inside a narrow lumen, so as to prevent the left and right slave arms 6L and 6R from coming into contact with the surrounding tissue with a strong force. On the other hand, the working space for the central slave arm 6C is limited, and normally, the joints of the central slave arm 6C do not need to be moved by large amounts.

According to this embodiment, because the master arms 11L and 11R have structures substantially similar to those of the left and right slave arms 6L and 6R, the operator Op can properly move the slave arms 6L and 6R while readily ascertaining the changing shapes of the slave arms 6L and 6R. Furthermore, the left and right slave arms 6L and 6R that move in a relatively large working space are used more frequently than the central slave arm 6C that moves in a limited working space. This embodiment allows for improved ease of used since it is provided with the master arms 11L and 11R having structures substantially similar to those of the frequently-used slave arms 6L and 6R.

In this embodiment, when the first control mode is to be switched to the second control mode, it is preferable that the controller 3 execute a reset flow prior to the start of the second control mode. In the reset flow, the controller 3 causes at least one of the central slave arm 6C and the master arms 11L and 11R to move so as to make the distal-end positions of the arms 6C and 11L or the arms 6C and 11R correspond with each other in the master space and the slave space.

The aforementioned reset flow may be performed manually by the operator Op manipulating the master arm 11L or 11R instead of being executed automatically by the controller 3. In this case, since it is difficult to make the distal-end positions of the arms 6C and 11L or the arms 6C and 11R perfectly correspond with each other, the controller 3 may terminate the reset flow when a deviation between the distal-end positions of the arms 6C and 11L or the arms 6C and 11R is within a predetermined range. Furthermore, in this case, the controller 3 may cause the display 12 to display an indication for guiding the operator Op to manipulate the master arm 11L or 11R.

Furthermore, in this embodiment, it is also preferable that the controller 3 execute a reset flow when the second control mode is to be switched to the first control mode. In this reset flow, the controller 3 causes at least one of the master arm 11L or 11R, for which the manipulation target has been changed, and the slave arm 6L or 6R serving as the manipulation target to move so as to make the rotational angles of the joints Ji and Ji' of the two arms match, thereby giving the two arms similar shapes.

This reset flow may also be performed manually by the operator Op instead of being executed automatically by the controller 3. In this case, since it is difficult to make the shapes of the two arms 6L and 11L or the two arms 6R and 11R perfectly correspond with each other, the controller 3 may terminate the reset flow when a deviation between the rotational angles of the joints Ji and Ji' of the two arms 6L and 11L or the two arms 6R and 11R is within a predetermined range. Furthermore, the controller 3 may cause the display 12 to display an indication for guiding the operator Op to manipulate the master arm 11L or 11R.

Furthermore, in this embodiment, the controller 3 may have at least two of the aforementioned second control mode and first to third modifications of the second control mode to be described below and may select an appropriate second control mode in accordance with the joint configuration of the central slave arm 6C.

Next, first to third modifications of the second control mode will be described.

Referring to FIG. 11, the first modification of the second control mode is to be used when the number of joints Ji' (i=1, 2, 3) of the central slave arm 6C is smaller than the number of joints Ji (i=1, 2, 3, 4) of each of the master arms 11L and 11R and when the joint configuration of the central slave arm 6C has a structure substantially similar to that of the joint configuration of a part of the master arm 11L or 11R.

In this mode, the controller 3 rotates the joints Ji' by amounts equal to the amounts of change θi in the corresponding joints Ji without taking into account the movement of the joint J4, which is included in the joints Ji of the master arm 11L or 11R and is an extra joint relative to the joints Ji' of the central slave arm 6C.

According to this mode, the operator Op can manipulate the master arm 11L or 11R while regarding the extra joint J4 of the master arm 11L or 11R as the distal end of the central slave arm 6C. In this case, the extra joint J4 may be secured with, for example, an actuator, a brake, or a clutch (not shown) so as to prevent an undesired movement thereof.

Figure 12:
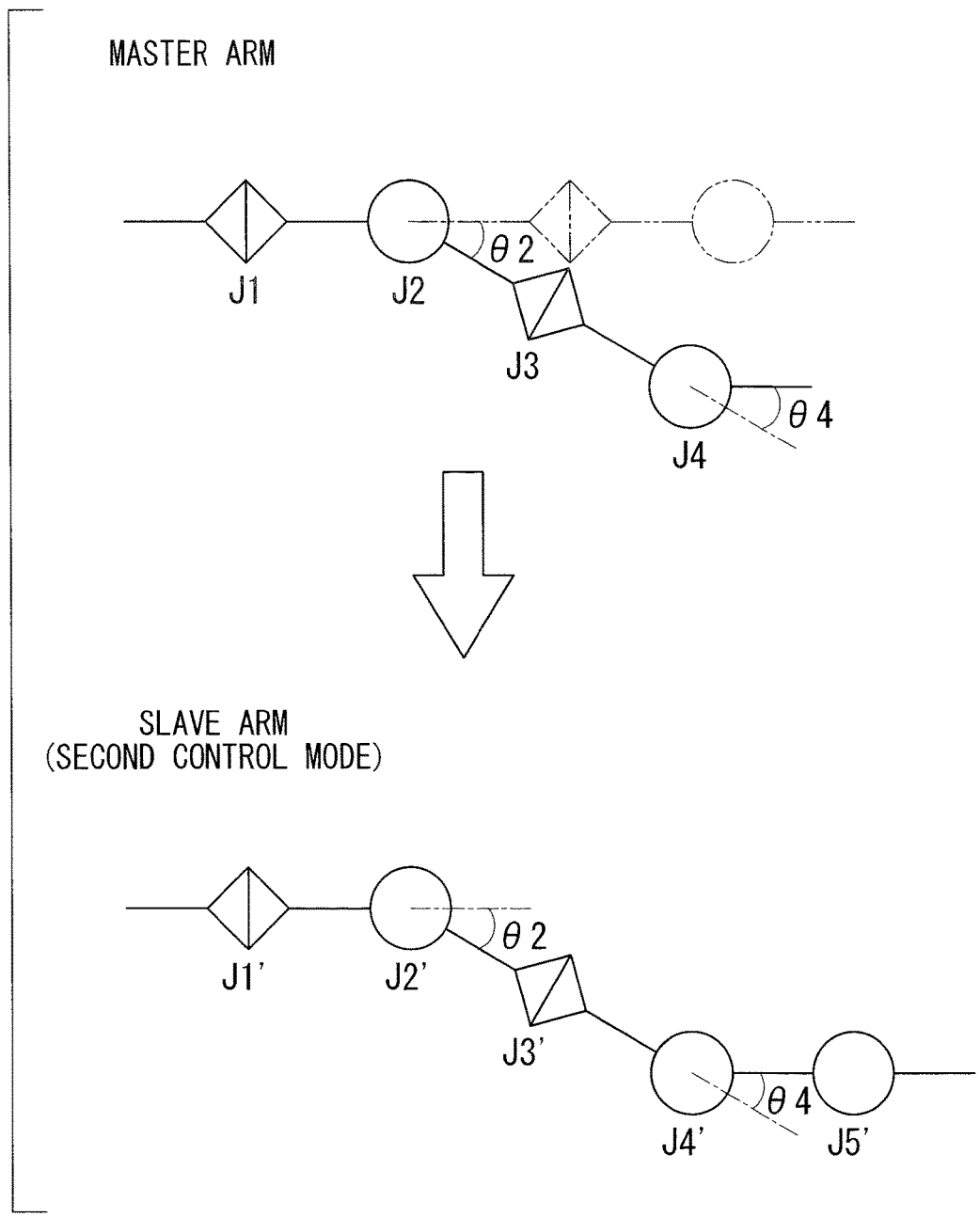
FIG. 12 illustrates the movement of the slave arms according to a second modification of the second control mode.

Referring to FIG. 12, the second modification of the second control mode is to be used when the number of joints Ji' (i=1, 2, 3, 4, 5) of the central slave arm 6C is larger than the number of joints Ji (i=1, 2, 3, 4) of each of the left and right master arms 11L and 11R and when a part of the joint configuration of the central slave arm 6C has a structure substantially similar to that of the joint configuration of the master arm 11L or 11R.

In this mode, the controller 3 rotates the joints Ji' of the central slave arm 6C that correspond to the joints Ji of the master arm 11L or 11R by amounts equal to the amounts of change θi in the joints Ji but does not control the joint J5', which is an extra joint relative to the joints Ji.

In this mode, the extra joint J5' may be secured with, for example, an actuator, a brake, or a clutch (not shown) so as to prevent an undesired movement thereof.

Furthermore, in this mode, at least one of the extra joint J5' and the joint J4' having a redundant relationship therewith may be selectively driven. Alternatively, the joint J4' and the joint J5' may both be driven such that the total driving amount is equal to the amount of change θ4 in the joint J4.

Figure 13:
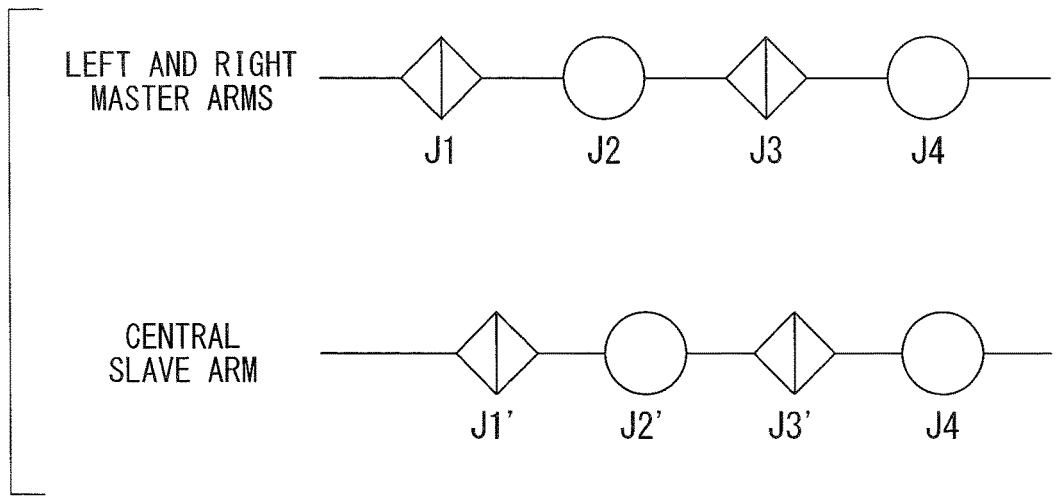
FIG. 13 schematically illustrates a joint configuration of a central slave arm according to a modification.

Referring to FIG. 13, the third modification of the second control mode is to be used when the central slave arm 6C has a joint arrangement in common with that of each of the left and right master arms 11L and 11R and when the ratio of distances between neighboring joints of the central slave arm 6C is different from that of the master arm 11L or 11R.

Figure 14A:
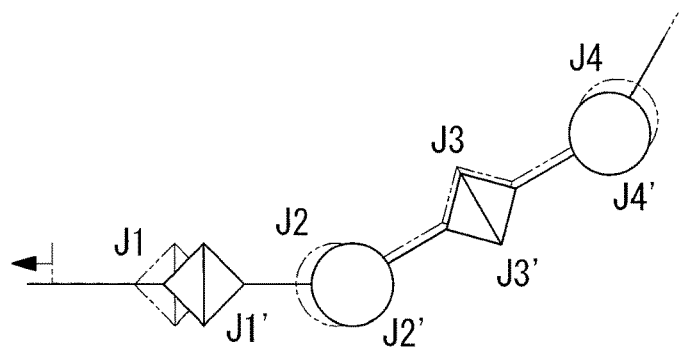
FIG. 14A illustrates the movement of the slave arms according to a third modification of the second control mode.

In this mode, the controller 3 moves the central slave arm 6C in a manner similar to FIG. 6. However, since the distances between the joints are different between the central slave arm 6C and the master arm 11L or 11R, the distal-end position of the central slave arm 6C becomes deviated from the distal-end position of the master arm 11L or 11R. Referring to FIG. 14A, the controller 3 causes the entire central slave arm 6C to advance or recede relative to the flexible section 4 so as to position the distal end of the central slave arm 6C on the same line as the distal-end portion of the master arm 11L or 11R.

Figure 14B:
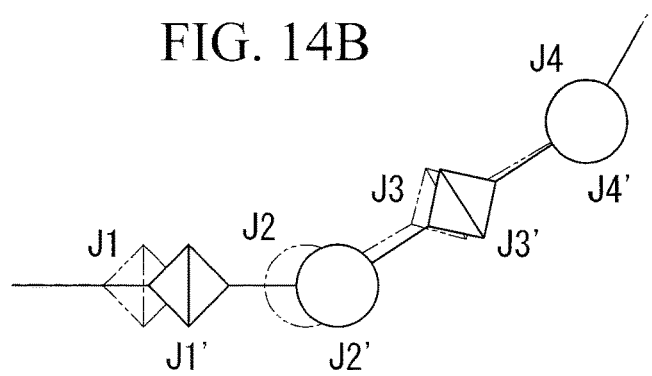
FIG. 14B illustrates another movement of the slave arms according to the third modification of the second control mode.

As shown in FIG. 14B, in this mode, the controller 3 may drive the central slave arm 6C so that the position and orientation of the joint J4' located at the most distal end correspond to those of the corresponding joint J4.

Figure 15:
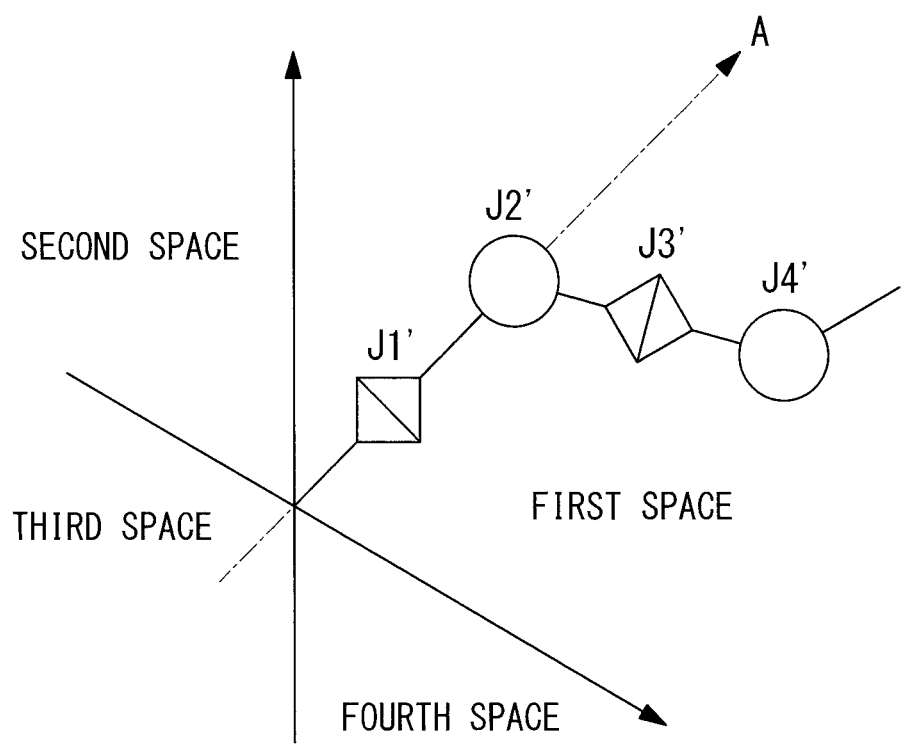
FIG. 15 illustrates another movement of the slave arms according to the third modification of the second control mode.

Furthermore, in this mode, if multiple solutions are obtained as a result of calculating the reverse kinematics of the central slave arm 6C on the basis of the movement amount of the distal end of the master arm 11L or 11R, the solution that causes the central slave arm 6C to be positioned in the same space as the master arm 11L or 11R from among first to fourth spaces may be used, as shown in FIG. 15. The first to fourth spaces are four spaces that are obtained by defining a central axis A of the base portion of each of the arms 6C, 11L, and 11R and that are divided by two orthogonal planes passing through the axis A.

Furthermore, although the slave manipulator 1 having the three slave arms 6L, 6R, and 6C attached to the distal end of the flexible section 4 is described in this embodiment, a specific configuration of the slave manipulator 1 is not limited to this. For example, two slave arms may be attached to the distal end of the flexible section 4. By using a single master arm, one of the slave arms may be controlled in accordance with the first control mode, and the other slave arm may be controlled in accordance with the second control mode. Alternatively, a single replaceable slave arm may be attached to the distal end of the flexible section 4. When the slave arm is replaced with another one, the switching operation between the first control mode and the second control mode may be performed on the basis of the joint configuration of that slave arm.

From the above-described embodiments and modifications thereof, the following aspects of the invention are derived.

A first aspect of the present invention provides a medical system including a first slave arm having joints; a master arm that has a joint configuration with a structure similar to a joint configuration of the first slave arm and that is operated by an operator; a second slave arm having joints; a manipulation-target switching unit that switches a manipulation target to be manipulated with the master arm between the first slave arm and the second slave arm; and a controller that controls the first slave arm and the second slave arm on the basis of an operation performed on the master arm. The controller switches between a first control mode and a second control mode in accordance with the joint configuration of the slave arm selected by the manipulation-target switching unit. The first control mode is a mode for controlling rotation of the joints of the first slave arm on the basis of rotation amounts of joints of the master arm so that the first slave arm has a shape similar to a shape of the master arm, and the second control mode is a mode for controlling rotation of the joints of the second slave arm on the basis of a movement of a predetermined section of the master arm so as to cause a predetermined section of the second slave arm to follow the movement of the predetermined section of the master arm.

According to the first aspect of the present invention, in the first control mode, the controller makes the first slave arm reproduce a movement corresponding to that of the master arm so that the operator can intuitively manipulate the first slave arm by using the master arm. In the second control mode, the controller makes the predetermined section of the second slave arm reproduce the movement of the predetermined section of the master arm so that the operator can intuitively manipulate the second slave arm having any joint configuration by using the master arm.

Accordingly, by switching between the first control mode and the second control mode in accordance with the joint configuration of the slave arm serving as the manipulation target to be manipulated with the master arm, a slave arm with a similar structure and a slave arm with a non-similar structure can both be dealt with using the same master arm, thereby eliminating the need for a dedicated master arm for each slave arm.

In the first aspect described above, when the controller transitions from the first control mode to the second control mode, the controller may execute a reset flow, prior to the second control mode, for moving at least one of the master arm and the second slave arm so that a position and orientation of the predetermined section of the master arm and a position and orientation of the predetermined section of the second slave arm correspond with each other.

Accordingly, since the second control mode starts in a state where the position and orientation of the predetermined section of the second slave arm match the position and orientation of the predetermined section of the master arm, manipulation of the second slave arm can be started smoothly.

In the first aspect described above, when the controller transitions from the second control mode to the first control mode, the controller may execute a reset flow, prior to the first control mode, for moving at least one of the master arm and the first slave arm so that displacement amounts of the joints of the master arm and displacement amounts of the joints of the slave arm correspond with each other.

Accordingly, since the first control mode starts in a state where the position and orientation of the entire first slave arm match the position and orientation of the entire master arm, manipulation of the first slave arm can be started smoothly.

In the first aspect described above, in the second control mode, the controller may control the rotation of the joints of the second slave arm on the basis of a movement amount of a distal end of the master arm so as to cause a distal end of the second slave arm to follow a movement of the distal end of the master arm.

Accordingly, the distal end of the second slave arm can be manipulated with high accuracy by using the master arm.

In the first aspect described above, in the second control mode, the controller may calculate reverse kinematics of the second slave arm on the basis of a movement amount of the distal end of the master arm and may select a solution with which a shape of the second slave arm is most similar to the shape of the master arm from among a plurality of solutions obtained.

Accordingly, the shape of the second slave arm can be roughly recognized on the basis of the master arm.

In the first aspect described above, in the second control mode, the controller may select a solution corresponding to a minimum total of differences between displacement amounts of the joints of the master arm and displacement amounts of the joints of the second slave arm.

Furthermore, in the present invention described above, assuming that four spaces are formed by being divided by two planes that pass through a central axis of a base portion of each of the second slave arm and the master arm and that are orthogonal to each other on the central axis, the controller may select a solution that causes the second slave arm to be positioned in a space corresponding to a space in which the master arm is positioned.

Accordingly, a solution that causes the shape and orientation of the second slave arm to be similar to the shape and orientation of the master arm can be selected by simple calculation.

In the first aspect described above, in the second control mode, the controller may control rotation of any of the joints of the second slave arm having corresponding joints existing in the master arm on the basis of rotation amounts of the joints of the master arm.

Accordingly, in a case where the number of joints is different between the master arm and the second slave arm, each corresponding pair of joints can be moved in a manner similar to the first control mode.

In the first aspect described above, a movement of a joint not having a corresponding joint among the joints included in the second slave arm and the master arm may be limited.

Accordingly, an undesired movement of a joint that is not to be controlled can be prevented.

In the first aspect described above, in the second control mode, the controller may cause the second slave arm to advance and recede so as to dispose a distal-end portion of the second slave arm at a position and orientation corresponding to a position and orientation of a distal-end portion of the master arm.

Accordingly, the distal end of the second slave arm can be made to follow the movement of the distal end of the master arm with high accuracy even when the distances between the joints are different between the master arm and the second slave arm.

In the first aspect described above, in the second control mode, the controller may control the second slave arm so that the joint located at a most distal end of the second slave arm is disposed at a position and orientation corresponding to a position and orientation of the joint located at a most distal end of the master arm.

Accordingly, the distal end of the second slave arm can be made to follow the movement of the distal end of the master arm with high accuracy even when the distances between the joints are different between the master arm and the second slave arm.

A second aspect of the present invention provides a control method for a medical system having a plurality of slave arms each having joints and a master arm operated by an operator. The control method includes alternately selecting a manipulation target to be manipulated with the master arm from among the plurality of slave arms; and switching between a first control mode and a second control mode in accordance with whether or not a joint configuration of the selected slave arm and a joint configuration of the master arm have structures similar to each other. The first control mode is a mode for controlling rotation of joints of the slave arm on the basis of rotation amounts of joints of the master arm so that the slave arm has a shape similar to a shape of the master arm. The second control mode is a mode for controlling the rotation of the joints of the slave arm on the basis of a movement of a predetermined section of the master arm so as to cause a predetermined section of the slave arm to follow the movement of the predetermined section of the master arm.

In the second aspect described above, when transitioning from the first control mode to the second control mode, a reset flow for moving at least one of the second slave arm and the master arm may be executed prior to the second control mode so that a position and orientation of the predetermined section of the second slave arm and a position and orientation of the predetermined section of the master arm correspond with each other.

In the second aspect described above, when transitioning from the second control mode to the first control mode, a reset flow for moving at least one of the first slave arm and the master arm may be executed prior to the first control mode so that displacement amounts of the joints of the first slave arm and displacement amounts of the joints of the master arm correspond with each other.

REFERENCE SIGNS LIST 1 slave manipulator
2 operation input unit
3 controller
4 flexible section
5 endoscope
6C central slave arm (second slave arm)
6L left slave arm (first slave arm)
6R right slave arm (first slave arm)
8C, 8L, 8R treatment sections
9 port
10 branch section
11L, 11R master arms
12 display
13 manipulation-target switching unit
100 medical system
J1 to J4, J1' to J5' joints
Op operator (operator)
P patient

The invention claimed is:

1. A medical system comprising:
a first slave arm having joints;
a master arm that has a joint configuration with a structure similar to a joint configuration of the first slave arm and that is operated by an operator;
a second slave arm having joints;
a manipulation-target switch that switches a manipulation target to be manipulated with the master arm between the first slave arm and the second slave arm; and
a controller comprising a processor comprising that controls the first slave arm and the second slave arm on the basis of an operation performed on the master arm,
wherein the controller switches between a first control mode and a second control mode in accordance with the joint configuration of the slave arm selected by the manipulation-target switch, the first control mode being a mode for controlling rotation of the joints of the first slave arm so that the joints of the first slave arm are rotated by rotation amounts equal to rotation amounts of joints of the master arm when the manipulation target is switched to the first slave arm by the manipulation-target switch, the second control mode being a mode for controlling rotation of the joints of the second slave arm on the basis of a movement of a predetermined section of the master arm so as to cause a predetermined section of the second slave arm to follow the movement of the predetermined section of the master arm.

2. A medical system comprising:
a first slave arm having joints;
a master arm that has a joint configuration with a structure similar to a joint configuration of the first slave arm and that is operated by an operator;
a second slave arm having joints;
a manipulation-target switch that switches a manipulation target to be manipulated with the master arm between the first slave arm and the second slave arm; and
a controller that controls the first slave arm and the second slave arm on the basis of an operation performed on the master arm,
wherein the controller switches between a first control mode and a second control mode in accordance with the joint configuration of the slave arm selected by the manipulation-target switch, the first control mode being a mode for controlling rotation of the joints of the first slave arm on the basis of rotation amounts of joints of the master arm so that the first slave arm has a shape similar to a shape of the master arm, the second control mode being a mode for controlling rotation of the joints of the second slave arm on the basis of a movement of a predetermined section of the master arm so as to cause a predetermined section of the second slave arm to follow the movement of the predetermined section of the master arm, and
wherein when the controller transitions from the first control mode to the second control mode, the controller executes a reset flow, prior to the second control mode, for moving at least one of the second slave arm and the master arm so that a position and orientation of the predetermined section of the second slave arm and a position and orientation of the predetermined section of the master arm correspond with each other.

3. A medical system comprising:
a first slave arm having joints;
a master arm that has a joint configuration with a structure similar to a joint configuration of the first slave arm and that is operated by an operator;
a second slave arm having joints;
a manipulation-target switch that switches a manipulation target to be manipulated with the master arm between the first slave arm and the second slave arm; and
a controller that controls the first slave arm and the second slave arm on the basis of an operation performed on the master arm,
wherein the controller switches between a first control mode and a second control mode in accordance with the joint configuration of the slave arm selected by the manipulation-target switch, the first control mode being a mode for controlling rotation of the joints of the first slave arm on the basis of rotation amounts of joints of the master arm so that the first slave arm has a shape similar to a shape of the master arm, the second control mode being a mode for controlling rotation of the joints of the second slave arm on the basis of a movement of a predetermined section of the master arm so as to cause a predetermined section of the second slave arm to follow the movement of the predetermined section of the master arm, and
wherein when the controller transitions from the second control mode to the first control mode, the controller executes a reset flow, prior to the first control mode, for moving at least one of the first slave arm and the master arm so that displacement amounts of the joints of the first slave arm and displacement amounts of the joints of the master arm correspond with each other.

4. A medical system comprising:
a first slave arm having joints;
a master arm that has a joint configuration with a structure similar to a joint configuration of the first slave arm and that is operated by an operator;
a second slave arm having joints;
a manipulation-target switch that switches a manipulation target to be manipulated with the master arm between the first slave arm and the second slave arm; and a controller that controls the first slave arm and the second slave arm on the basis of an operation performed on the master arm, wherein the controller switches between a first control mode and a second control mode in accordance with the joint configuration of the slave arm selected by the manipulation-target switch, the first control mode being a mode for controlling rotation of the joints of the first slave arm on the basis of rotation amounts of joints of the master arm so that the first slave arm has a shape similar to a shape of the master arm, the second control mode being a mode for controlling rotation of the joints of the second slave arm on the basis of a movement of a predetermined section of the master arm so as to cause a predetermined section of the second slave arm to follow the movement of the predetermined section of the master arm, wherein, in the second control mode, the controller controls the rotation of the joints of the second slave arm on the basis of a movement amount of a distal end of the master arm so as to cause a distal end of the second slave arm to follow a movement of the distal end of the master arm, and wherein, in the second control mode, the controller calculates reverse kinematics of the second slave arm on the basis of a movement amount of the distal end of the master arm and selects a solution with which a shape of the second slave arm is most similar to the shape of the master arm from among a plurality of solutions obtained.

5. The medical system according to claim 4,
wherein, in the second control mode, the controller selects a solution corresponding to a minimum total of differences between displacement amounts of the joints of the master arm and displacement amounts of the joints of the second slave arm.

6. The medical system according to claim 4,
wherein, assuming that four spaces are formed by being divided by two planes that pass through a central axis of a base portion of each of the second slave arm and the master arm and that are orthogonal to each other on the central axis, the controller selects a solution that causes the second slave arm to be positioned in a space corresponding to a space in which the master arm is positioned.

7. A medical system comprising:
a first slave arm having joints;
   a master arm that has a joint configuration with a structure similar to a joint configuration of the first slave arm and that is operated by an operator;
   a second slave arm having joints;
   a manipulation-target switch that switches a manipulation target to be manipulated with the master arm between the first slave arm and the second slave arm; and
   a controller that controls the first slave arm and the second slave arm on the basis of an operation performed on the master arm,
   wherein the controller switches between a first control mode and a second control mode in accordance with the joint configuration of the slave arm selected by the manipulation-target switch, the first control mode being a mode for controlling rotation of the joints of the first slave arm on the basis of rotation amounts of joints of the master arm so that the first slave arm has a shape similar to a shape of the master arm, the second control mode being a mode for controlling rotation of the joints of the second slave arm on the basis of a movement of a predetermined section of the master arm so as to cause a predetermined section of the second slave arm to follow the movement of the predetermined section of the master arm, and
   wherein, in the second control mode, the controller controls rotation of any of the joints of the second slave arm having corresponding joints existing in the master arm on the basis of rotation amounts of the joints of the master arm.

8. The medical system according to claim 7,
wherein the controller limits a movement of a joint not having a corresponding joint among the joints included in the second slave arm and the master arm.

9. A control method for a medical system having a plurality of slave arms each having joints and a master arm operated by an operator, the control method comprising:
   alternately selecting a manipulation target to be manipulated with the master arm from among the plurality of slave arms; and
   switching between a first control mode and a second control mode in accordance with whether or not a joint configuration of a selected slave arm, the selected slave arm selected from the plurality of slave arms, and a joint configuration of the master arm have structures similar to each other, the first control mode being a mode for controlling rotation of joints of the selected slave arm so that the joints of the selected slave arm are rotated by rotation amounts equal to rotation amounts of joints of the master arm, the second control mode being a mode for controlling the rotation of the joints of another of the plurality of slave arms on the basis of a movement of a predetermined section of the master arm so as to cause a predetermined section of the slave arm to follow the movement of the predetermined section of the master arm.

10. The control method for a medical system according to claim 9,
wherein, when transitioning from the first control mode to the second control mode, a reset flow for moving at least one of the second slave arm and the master arm is executed prior to the second control mode so that a position and orientation of the predetermined section of the second slave arm and a position and orientation of the predetermined section of the master arm correspond with each other.

11. The control method for a medical system according to claim 9,
wherein, when transitioning from the second control mode to the first control mode, a reset flow for moving at least one of the first slave arm and the master arm is executed prior to the first control mode so that displacement amounts of the joints of the first slave arm and displacement amounts of the joints of the master arm correspond with each other.

* * * * *